(12) United States Patent
Lockhart

(10) Patent No.: US 6,436,066 B1
(45) Date of Patent: Aug. 20, 2002

(54) TRUSS BODY JOINT BRACE

(76) Inventor: Robert Lockhart, 6183 Montgomery Pl., San Jose, CA (US) 95135

( * ) Notice: Subject to any disclaimer, the term of this patent is extended or adjusted under 35 U.S.C. 154(b) by 0 days.

(21) Appl. No.: 09/497,828

(22) Filed: Feb. 3, 2000

(51) Int. Cl.[7] .............................. A61F 5/00; A61F 13/00
(52) U.S. Cl. ........................................ 602/26; 602/62
(58) Field of Search .................... 602/5, 19, 20–21, 602/23, 26, 60–63; 128/878–879, 881–882, 95.1, 121.1; 2/22, 24, 44, 110, 105, 326; 450/2, 19, 74, 85, 96, 107, 115, 137, 132, 130

(56) References Cited

U.S. PATENT DOCUMENTS

| 1,092,836 A | * | 4/1914 | Hart |
| 3,387,305 A | * | 6/1968 | Shafer ............................. 2/22 |
| 4,887,590 A | * | 12/1989 | Logue et al. ............. 128/80 C |
| 4,938,206 A | * | 7/1990 | Harris et al. ............. 128/80 F |
| 5,016,621 A | * | 5/1991 | Bender ..................... 128/80 C |
| 5,306,230 A | * | 4/1994 | Bodine ........................ 602/26 |
| 5,512,039 A | | 4/1996 | White |
| 5,599,288 A | | 2/1997 | Shirley et al. |
| 5,782,785 A | | 7/1998 | Herzberg |
| 5,797,864 A | | 8/1998 | Taylor |
| 5,857,988 A | | 1/1999 | Shirley |

* cited by examiner

*Primary Examiner*—Denise M. Pothier
(74) *Attorney, Agent, or Firm*—Thomas M. Freiburger

(57) ABSTRACT

The present truss body joint brace includes a pair of upper bars for positioning on opposite sides of an upper portion of a limb, a pair of lower bars for positioning on opposite sides of a lower portion of the limb, and a pair of hinges for positioning on opposite sides of a joint on the limb and connected between respective upper bars and respective lower bars. A pair of upper front crossed straps and a pair of upper back crossed straps are connected between the upper bars. A pair of lower front crossed straps and a pair of lower back crossed straps are connected between the lower bars. A flexible tubular upper sleeve is positioned between the upper bars, and a flexible tubular lower sleeve is positioned between the lower bars. The straps are adjustable in length for a snug fit. The bars, crossed straps, and the limb cooperate to form a truss structure that strongly resists lateral forces and protect the body joint from injury while allowing normal joint movement.

14 Claims, 3 Drawing Sheets

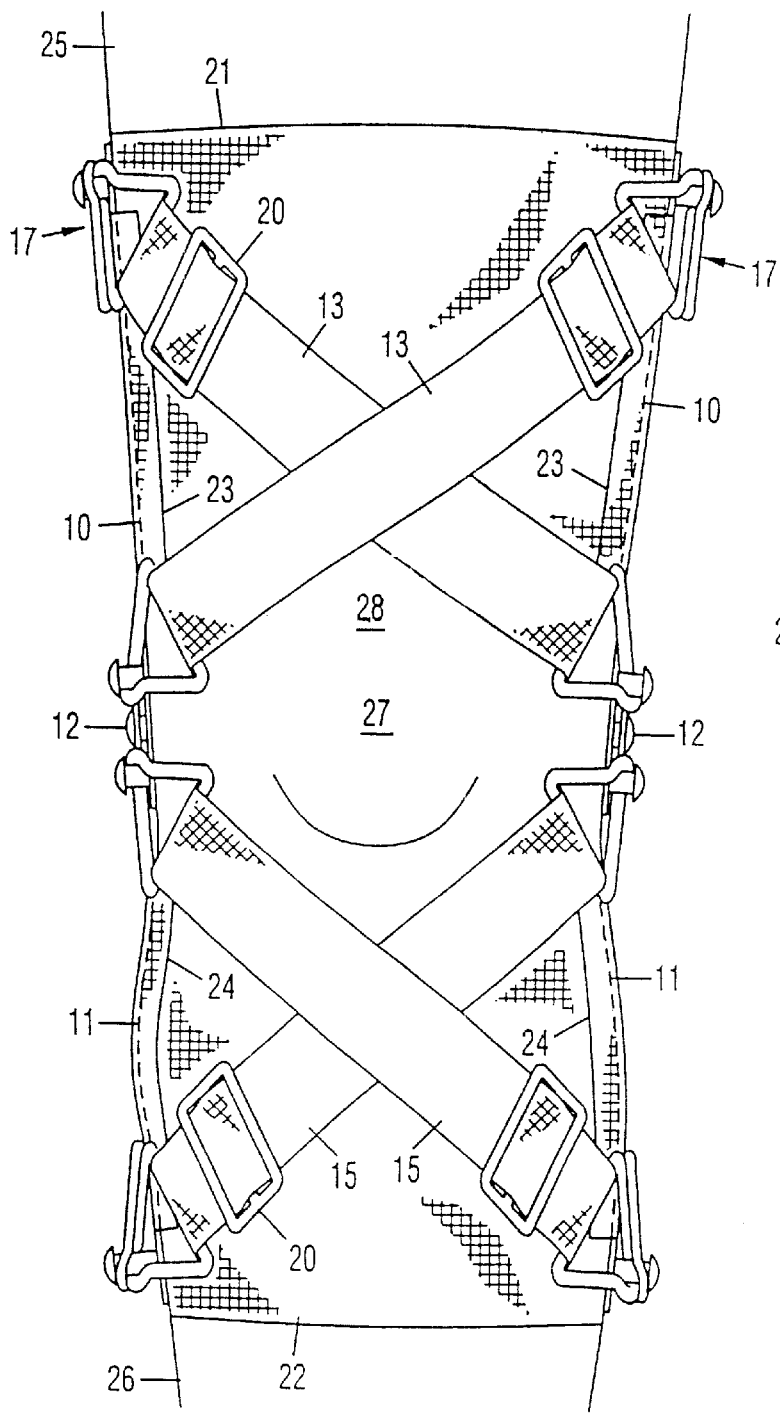
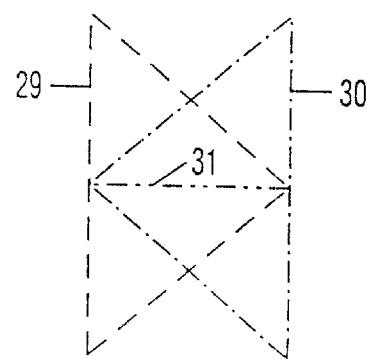
Fig. 3
Fig. 4

TRUSS BODY JOINT BRACE

BACKGROUND OF THE INVENTION

1. Field of the Invention

This invention relates generally to knee braces.

2. Prior Art

Knee braces are known for reducing stress on a knee by spreading forces over a wide area on the leg. They fall into two categories: flexible braces, and rigid braces. A flexible knee brace disclosed in U.S. pat. No. 5,512,039 to White is comprised of a tubular sleeve surrounded by flexible reinforcing straps. It is for tightly holding the muscles and ligaments in position, and also for keeping warm. It does not provide any structural support, so the knee is still prone to injury from excess stress. It must be wrapped tightly to stay in position, so that it is uncomfortable to wear. Although it is flexible, the sturdiness of its materials makes it difficult to bend, so that it hinders leg movements.

A rigid brace disclosed in U.S. pat. No. 5,857,988 to Shirley is comprised of a pair of upper rods connected to a pair of lower rods by respective hinges. The rods are strapped to opposite sides of a leg with the hinges positioned on the sides of the knee. The loads on the ligaments can be varied by adjusting the tension of a pair of cables zigzagging between the upper and lower bars at the front of the brace. The rods are connected by horizontal straps at the back of the brace. The asymmetry between the front and the back of the brace results in uneven load distribution wherein some parts of the leg are subject to higher forces than others. Further, the cables are disconnected from each other. They act independently of each other, so that they do not help resist lateral forces.

A similar brace disclosed in U.S. pat. No. 5,782,785 to Herzberg includes horizontal straps connecting the rods on opposite sides of the leg. The horizontal straps do not help resist lateral forces.

Another rigid brace disclosed in U.S. pat. No. 5,797,864 to Taylor includes rods on only one side of the leg. The knee is tensioned against the rods by a single helical strap connected between the upper and lower rods and wrapped around the other side of the knee. The back of the knee is crossed by the strap, which hinders bending of the leg. Because of the severe asymmetry of the brace, lateral forces tend to twist the knee and loosen the brace.

The resistance of prior art rigid braces against lateral forces depends entirely on the rigidity of the rods. The straps between the rods do not contribute to lateral rigidity. The rods can be made thick and strong enough to provide enough lateral rigidity, but the benefits are offset by an accompanying increase in bulk and weight. The discomfort associated with prior art rigid braces makes them especially undesirable to wear prior to injury for injury prevention.

OBJECTIVES OF THE INVENTION

Accordingly, the objectives of the present truss body joint brace are:

- to reduce stress on a body joint by spreading lateral forces over a large area on a limb;
- to strongly resist lateral forces;
- to minimize interference with limb movements;
- to be comfortable to wear;
- to stay in position without a tight fit;
- to be easily adjustable for fitting different wearers;
- to be easily adjustable for accommodating changes in the shape or size of the limb;
- to be very lightweight for comfort;
- to be compact and thus cosmetically pleasing; and
- to be inexpensive.

Further objectives of the present invention will become apparent from a consideration of the drawings and ensuing description.

BRIEF SUMMARY OF THE INVENTION

The present truss body joint brace includes a pair of upper bars for positioning on opposite sides of an upper portion of a limb, a pair of lower bars for positioning on opposite sides of a lower portion of the limb, and a pair of hinges for positioning on opposite sides of a joint on the limb and connected between respective upper bars and respective lower bars. A pair of upper front crossed straps and a pair of upper back crossed straps are connected between the upper bars. A pair of lower front crossed straps and a pair of lower back crossed straps are connected between the lower bars. A flexible tubular upper sleeve is positioned between the upper bars, and a flexible tubular lower sleeve is positioned between the lower bars. The straps are adjustable in length for a snug fit. The bars, crossed straps, and the limb cooperate to form a truss structure that strongly resists lateral forces and protect the body joint from injury.

BRIEF DESCRIPTION OF THE SEVERAL VIEWS OF THE DRAWING

FIG. 3 is a front view thereof when worn on the limb.

FIG. 4 is a representation of a truss structure formed by the present body joint brace.

DETAILED DESCRIPTION OF THE INVENTION

Figure 1:
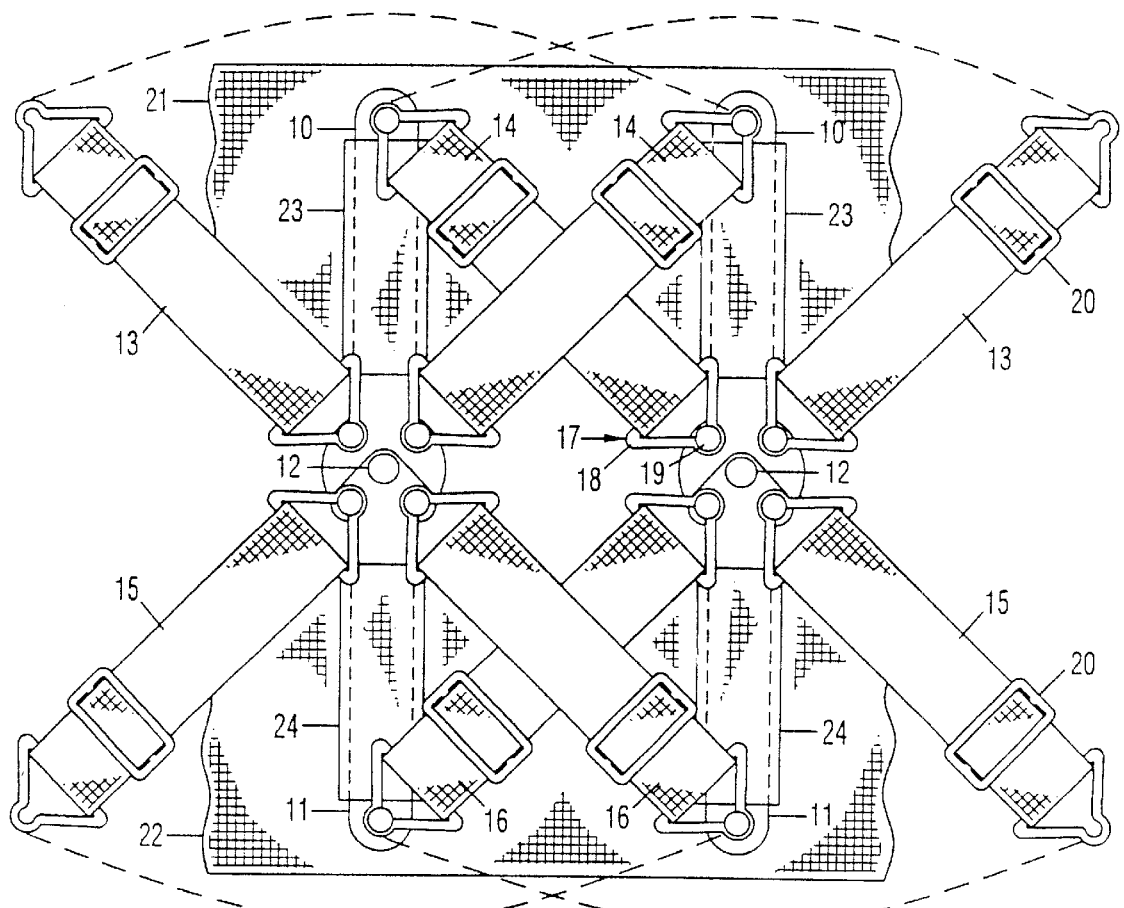
FIG. 1 is an outside view of the present truss body joint brace when spread open and laid flat.

FIG. 1:

A preferred embodiment of the present truss body joint brace is shown in an outside view spread open and laid flat in FIG. 1. It includes a pair of generally rigid upper bars 10 for positioning on opposite sides of an upper portion of a limb, a pair of generally rigid lower bars 11 for positioning on opposite sides of a lower portion of the limb, and a pair of hinges 12 positioning on opposite sides of a joint on the limb and connecting respective upper bars 10 to respective lower bars 11. Upper bars 10 and lower bars 11 are preferably made of a material rigid enough to resist compressive forces during use, but also bendable enough for being adjusted to conform to the contours of the limb and thus are referred to as generally rigid. Hinges 12 are preferably ball-bearing hinges for strength and smoothness, but other suitable types of hinges may be used.

A pair of flexible upper front crossed straps 13 and a pair of flexible upper back crossed straps 14 are connected between upper bars 10. A pair of flexible lower front crossed straps 15 and a pair of flexible lower back crossed straps 16 are connected between lower bars 11. The straps are preferably connected to the bars with hinged connectors 17, which are preferably comprised of connecting buckles 18 on opposite ends of each strap detachably connected to pivots 19 on the bars. Alternatively, the hinged connectors may be of another type, or non-hinged connectors may be used. A mix of detachable and non-detachable connectors may also be used. For example, upper front straps 13 and lower front straps 15 may be detachable for putting on and taking off the body joint brace, whereas upper back straps 14 and lower back straps 16 may be permanently attached. Each strap is preferably adjustable in length for fitting different users and for fine tuning a fit, preferably by having a slide buckle 20.

A flexible tubular upper sleeve 21 is positioned between upper bars 10, and a flexible tubular lower sleeve 22 is positioned between lower bars 11. Sleeves 21 and 22 are preferably permanently arranged in tubular shapes, but are shown broken and laid flat for clarity. Alternatively, sleeves 21 and 22 may each include a separable joint so they may be opened for entry and exit. Upper bars 10 and lower bars 11 are respectively secured within upper pockets 23 and lower pockets 24 on upper sleeve 21 and lower sleeve 22.

Figure 2:
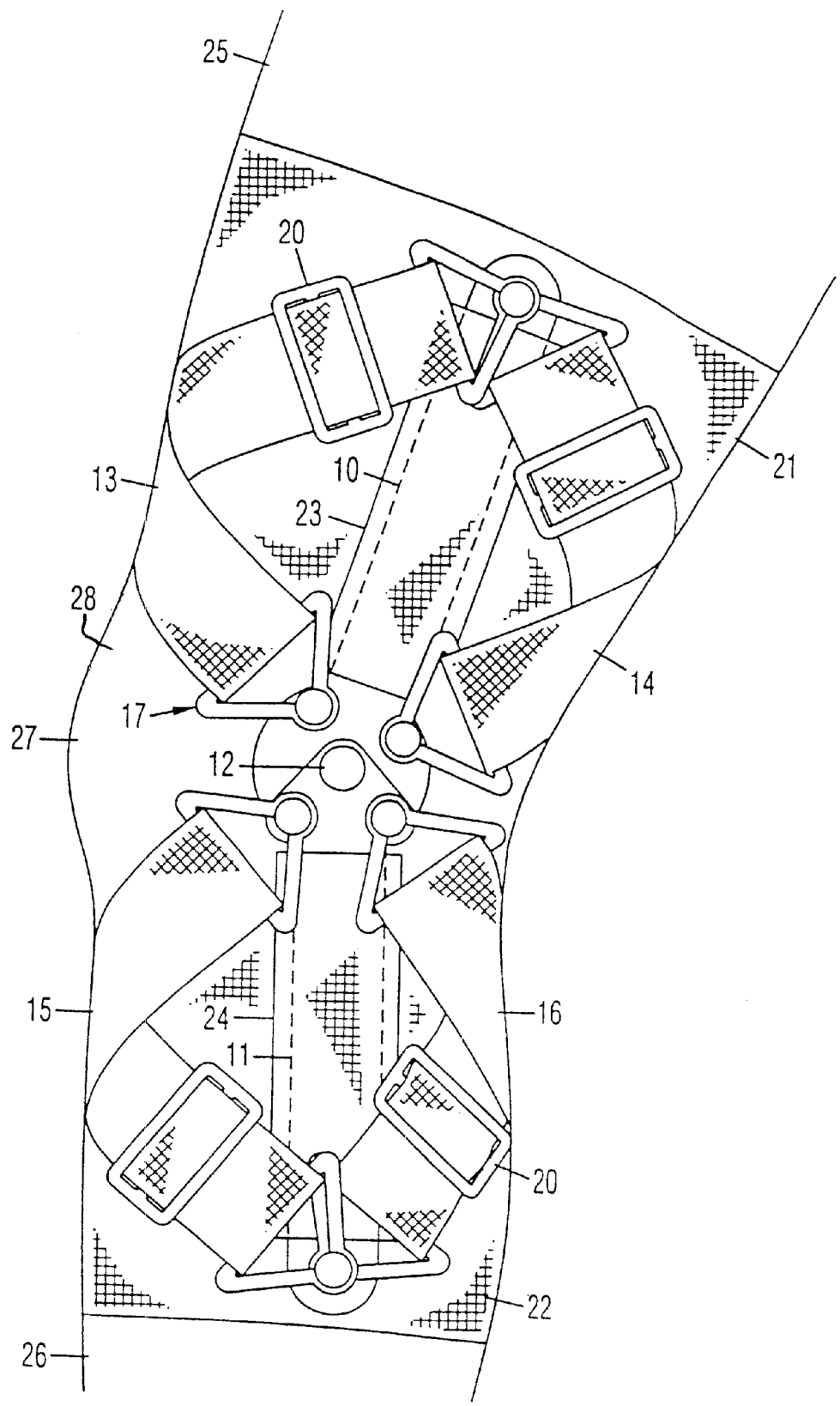
FIG. 2 is a side view thereof when worn on a limb.

FIGS. 2–4:

The truss body joint brace is shown worn on a limb in a side view in FIG. 2 and in a front view in FIG. 3. As an example, a leg at the knee joint is shown, but the brace may be adapted for bracing other body joints, such as the ankles and elbows. The brace is put on by loosening or unbuckling front crossed straps 13 and 15, and slipping the limb through tubular sleeves 21 and 22. Upper sleeve 21 is positioned around an upper portion 25 of a limb, lower sleeve 22 is positioned around a lower portion 26 of the limb, and hinges 12 are positioned on the sides of a joint 27 on the limb. Front crossed straps 13 and 15 are respectively buckled to bars 10 and 11, and the tension in the straps is adjusted as necessary for a snug fit. Upper bars 10 and lower bars 11 are bent to conform to the shape of the limb. Sleeves 21 and 22 protect the skin from being chafed by the bars and straps, and are preferably elastic for preventing slipping.

There are no straps connected between upper bars 10 and lower bars 11, that is, there are no straps crossing the back of the knee to interfere with limb movements, so that the limb can freely bend with little effort. Upper front straps 13 and lower front straps 15 cooperate to form a diamond-shaped opening 28 that frames the protruding joint and prevents the brace from slipping down on the limb. Thus the brace stays in position without an extremely tight fit, so that it is comfortable to wear.

The brace is generally symmetrical between its front and back, as shown in FIG. 2, and between its sides, as shown in FIG. 3. Due to the general symmetry, loads are distributed evenly over a wide area on the limb to significantly reduce the chance of injury. The bars, crossed straps, and limb form a truss structure comprised of two opposite simple trusses 29 and 30 that are connected together, as shown in FIG. 4. Trusses 29 and 30 combine to strongly resist lateral forces from either side. Each simple truss, which is a geometric term, is comprised of two opposing right triangles positioned in a vertical column and sharing a common side 31 which is comprised of the wearer's limb. The truss structure has a high strength-to-weight ratio, so that the brace can be strong but still slim and lightweight. The brace is thus comfortable enough to wear prior to injury for injury prevention, even when people are much less motivated to wear a brace.

Accordingly, the present truss body joint brace reduces stress on a body joint by spreading forces over a large area on the limb. It strongly resists lateral forces. It minimizes interference with limb movements. It is comfortable to wear. It stays in position without a very tight fit. It is easily adjustable for fitting different wearers. It is very lightweight for comfort. It is compact and thus cosmetically pleasing. It is simple and inexpensive to produce.

Although the above description is specific, it should not be considered as a limitation on the scope of the invention, but only as an example of the preferred embodiment. Many variations are possible within the teachings of the invention. Therefore, the scope of the invention should be determined by the appended claims and their legal equivalents, not by the examples given.

I claim:

1. A truss body joint brace, comprising:
   a pair of generally rigid upper bars for positioning on opposite sides of an upper portion of a limb;
   a pair of generally rigid lower bars for positioning on opposite sides of a lower portion of said limb;
   a pair of hinges for positioning on opposite sides of a joint connecting said upper portion of said limb to said lower portion of said limb, said hinges connecting respective ones of said upper bars to respective ones of said lower bars;
   a pair of upper front crossed straps extending between and fixed to said upper bars for positioning on a front of said upper portion of said limb;
   a pair of upper back crossed straps extending between and fixed to said upper bars for positioning on a back of said upper portion of limb;
   a pair of lower front crossed straps extending between and fixed to said lower bars for positioning on a front of said lower portion of said limb; and
   a pair of lower back crossed straps extending between and fixed to said lower bars for positioning on a back of said lower portion of said limb;
   whereby said pairs of crossed straps, said upper bars and said lower bars form truss structures to resist lateral forces and protect said joint from injury.

2. The truss body joint brace of claim 1, wherein said hinges are comprised of ball-bearing hinges for strength and smoothness.

3. The truss body joint brace of claim 1, wherein said upper front crossed straps, said upper back crossed straps, said lower front crossed straps, and said lower back crossed straps are comprised of flexible straps which are adjustable in length for fitting different users and for fine tuning a fit.

4. The truss body joint brace of claim 1, wherein respective opposite ends of said upper front crossed straps and said upper back crossed straps are hinged to said upper bars, and respective opposite ends of said lower front crossed straps and said lower back crossed straps are hinged to said lower bars.

5. The truss body joint brace of claim 1, further including a flexible tubular upper sleeve positioned between said upper bars for wrapping around said upper portion of said limb, and a flexible tubular lower sleeve positioned between said lower bars for wrapping around said lower portion of said limb.

6. The truss body joint brace of claim 5, further including a pair of upper pockets on said upper sleeve and a pair of lower pockets on said lower sleeve, said upper bars being secured in respective ones of said upper pockets, and said lower bars being secured in respective ones of said lower pockets.

7. A truss body joint brace, comprising:
   a pair of generally rigid upper bars for positioning on opposite sides of an upper portion of a limb;
   a pair of generally rigid lower bars for positioning on opposite sides of a lower portion of said limb;
   a pair of hinges for positioning on opposite sides of a joint connecting said upper portion of said limb to said lower portion of said limb, said hinges connecting respective ones of said upper bars to respective ones of said lower bars;

a pair of upper front crossed straps connected between said upper bars for positioning on a front of said upper portion of said limb;

a pair of upper back crossed straps connected between said upper bars for positioning on a back of said upper portion of said limb;

a pair of lower front crossed straps connected between said lower bars for positioning on a front of said lower portion of said limb;

a pair of lower back crossed straps connected between said lower bars for positioning on a back of said lower portion of said limb;

a flexible tubular upper sleeve positioned between said upper bars for wrapping around said upper portion of said limb;

a flexible tubular lower sleeve positioned between said lower bars for wrapping around said lower portion of said limb; and a diamond-shaped opening between said upper front crossed straps and said lower front crossed straps for framing said joint and preventing slippage;

whereby said truss body joint brace is arranged to resist lateral forces and protect said joint from injury.

8. The truss body joint brace of claim 7, wherein said hinges are comprised of ball-bearing hinges for strength and smoothness.

9. The truss body joint brace of claim 7, wherein said upper front crossed straps, said upper back crossed straps, said lower front crossed straps, and said lower back crossed straps are comprised of flexible straps which are adjustable in length for fitting different users and for fine tuning a fit.

10. The truss body joint brace of claim 7, wherein respective opposite ends of said upper front crossed straps and said upper back crossed straps are hinged to said upper bars, and respective opposite ends of said lower front crossed straps and said lower back crossed straps are hinged to said lower bars.

11. The truss body joint brace of claim 7, further including a pair of upper pockets on said upper sleeve, and a pair of lower pockets on said lower sleeve, said upper bars being secured in respective ones of said upper pockets, and said lower bars being secured in respective ones of said lower pockets.

12. A truss knee brace for bracing the knee joint of a leg against lateral bending, comprising:

first and second pivotal hinges for positioning on opposite sides of the knee joint;

at least one upper truss connected to the hinges and sized and configured to be positioned on an upper portion of the leg, above the knee, at least one lower truss connected to the hinges and sized and configured to be positioned on a lower portion of the leg, below the knee, at least two generally rigid bars including an upper bar secured to and extending up from an upper part of said first hinge, and a lower bar directly below the upper bar, secured to and extending down from a lower part of said first hinge, the upper and lower bars forming parts of the upper truss and the lower truss, respectively, the upper truss including two upper straps secured to an upper end of the upper bar and configured so as to extend down and around the leg, away from one another, and both upper straps being connected to an upper part of said second hinge opposite said first hinge, the lower truss including two lower straps secured to a lower end of the lower bar and configured so as to extend up and around the leg, away from one another, and both lower straps being connected to a lower part of the second hinge opposite said first hinge, whereby the knee brace when worn on a leg resists lateral bending of the knee joint from a force tending to push on the knee at said first hinge, through tension and compression in the upper and lower trusses, the bars going into compression and the straps going into tension to resist said lateral bending of the knee joint.

13. The truss knee brace of claim 11, further including upper and lower tubular sleeves sized and configured to be secured around upper and lower portions of the leg just above and below the knee joint, the bars being secured to the sleeves.

14. The truss knee brace of claim 11, wherein at least some of said straps comprise flexible straps adjustable in length for fitting different users.

* * * * *